United States Patent [19]
Erickson

[11] Patent Number: 5,409,508
[45] Date of Patent: Apr. 25, 1995

[54] MEANS AND METHOD FOR ENHANCING PLANT GROWTH UNDER FIELD CONDITIONS

[75] Inventor: Stewart E. Erickson, Ketchum, Id.

[73] Assignee: SEEC, Inc., Mendota Heights, Minn.

[21] Appl. No.: 137,384

[22] Filed: Oct. 18, 1993

Related U.S. Application Data

[63] Continuation of Ser. No. 601,873, Oct. 23, 1990, abandoned.

[51] Int. Cl.⁶ ............................................. A01G 9/00
[52] U.S. Cl. ........................................ 47/1.01; 47/17
[58] Field of Search ................................... 47/17, 1.01

[56] References Cited

U.S. PATENT DOCUMENTS

| | | | |
|---|---|---|---|
| 3,479,825 | 11/1969 | Hellstrom | 47/1.01 |
| 3,647,411 | 3/1972 | Stevens . | |
| 3,925,928 | 12/1975 | Constantinescu et al. | 47/17 |
| 3,961,446 | 6/1976 | Mason, Jr. et al. | 47/38 |
| 3,997,405 | 12/1976 | Muller et al. . | |
| 3,999,329 | 12/1976 | Brais . | |
| 4,003,160 | 1/1977 | Muller et al. . | |
| 4,028,847 | 6/1977 | Davis et al. . | |
| 4,073,089 | 2/1978 | Maginnes et al. | 47/17 |
| 4,178,715 | 12/1979 | Greenbaum | 47/17 |
| 4,327,521 | 5/1982 | Mason, Jr. et al. . | |
| 4,486,977 | 12/1984 | Edgecombe et al. . | |
| 4,689,067 | 8/1987 | Küchens et al. . | |
| 4,817,332 | 4/1989 | Ikeda et al. | 47/17 |

FOREIGN PATENT DOCUMENTS 2264087  10/1975  France .

OTHER PUBLICATIONS

Soviet Inventions Illustrated, Section PQ, Week 8419, 20 Jun. 1984, Derwent Publications, Ltd. (SU-A-1 034 623 (Shaburyan SS) 15 Aug. 1983, Abstract.
Soviet Inventions Illustrated, Section PQ, Week 9126, 14 Aug. 1991, Derwent Publications Ltd. (SU-A-1 586 557 Agro-Forest Meloir) 23 Aug. 1990, Abstract.
Soviet Inventions Illustrated, Section PQ, Week 9106, 27 Mar. 1991, Derwent Publications Ltd. (SU-A-1 549 492 Agaponov N N) 15 Mar. 1990, Abstract.
Soviet Inventions Illustrated, Section PQ, Week 9114, 22 May 1991, Derwent Publications Ltd. (SU-A-1 565 361 OMSK Agric Inst) 23 May 1990, Abstract.

*Primary Examiner*—Ramon S. Britts
*Assistant Examiner*—Joanne C. Downs
*Attorney, Agent, or Firm*—Fredrikson & Byron

[57] ABSTRACT

An economic and practical system for enhancing plant growth by delivering gaseous carbon dioxide to the plants. The vegetation is planted within an elongated trench preferably in an overstocked condition whereby the vegetation is permitted to grow sufficiently to define a closed canopy. The carbon dioxide-rich gas may be delivered to the trench by conduits beneath the level of the canopy. The trenches can include a floor and side walls which extend vertically upwardly and divergently from each other to restrict the flow of air beneath the canopy thereby minimizing the dilutive effects of the atmosphere. The trenches can also be oriented generally perpendicularly to the prevailing wind direction to minimize the tendency of the wind to carry off the carbon dioxide.

15 Claims, 2 Drawing Sheets

MEANS AND METHOD FOR ENHANCING PLANT GROWTH UNDER FIELD CONDITIONS

This application is a continuation of application Ser. No. 07/601,873, filed Oct. 23, 1990, abandoned.

BACKGROUND OF THE INVENTION

The present invention relates generally to a system for enhancing plant growth under field conditions. Although the teachings of this invention may be used to increase the rate of plant growth in a wide number of applications, the invention is particularly well suited for use in reforestation of land.

It is well known that plants utilize carbon dioxide in the surrounding atmosphere as a source of carbon from which the complex organic molecules making up the plant are formed. Plants absorb the carbon dioxide through stomates in their leaves and release free oxygen after the photosynthesis process breaks the carbon dioxide into its component elements.

It has long been known that the growth rate of plants generally bears a proportional relationship to the concentration of carbon dioxide in the ambient atmosphere—a low carbon dioxide concentration tends to stunt the growth of the plant while an enhanced carbon dioxide concentration can significantly increase the rate at which the plants grow. Under normal atmospheric conditions, air generally comprises about 78% nitrogen, about 21% oxygen and only about 0.03% carbon dioxide, with the balance being made up of a number of trace gases. By significantly increasing this minimal carbon dioxide concentration adjacent the vegetation, one would expect to see a correspondingly significant increase in the vegetation's rate of development.

This relationship between carbon dioxide concentration and the growth rate of plants has been exploited for quite some time in greenhouse environments. For examples of greenhouse systems which utilize enhanced carbon dioxide concentration, see, e.g., U.S. Pat. Nos. 3,999,329 (Brais), 4,028,847 (Davis, et al), and 4,073,089 (Maginnes, et al). Although this technique seems to work quite well in an enclosed environment, such as that presented by a greenhouse, utility of this technique of growing plants under field conditions is severely limited.

When growing plants out-of-doors, it has heretofore been very impractical to supply gaseous carbon dioxide over large areas. When gaseous carbon dioxide is supplied under field conditions, the carbon dioxide becomes diluted by the ambient atmosphere and blown away by the wind. Some inventors have attempted to circumvent these difficulties by dissolving high concentrations of carbon dioxide in aqueous solution and spraying this solution directly on the plants. (See, e.g., U.S. Pat. No. 4,689,067, issued to Kückens, et al.) As the water evaporates or is absorbed by the plants, gaseous carbon dioxide is liberated very near the stomates. By releasing the carbon dioxide in such close proximity to the stomates, the dilutive effects of the atmosphere and the tendency of wind to carry off the carbon dioxide are minimized. For an example of such a method see U.S. Pat. No. 4,689,067 (Kückens et al)

As plants absorb carbon dioxide from the ambient air, the supply of carbon dioxide in that air is obviously diminished. Under many field conditions, such as those most commonly encountered in fields of commercially-grown agricultural products, there is sufficient circulation of air adjacent the plants to ensure a relatively constant supply of carbon dioxide to the entire leaf system of the plant. In certain circumstances, however, there is insufficient circulation of air across the plants.

Limited air circulation is most often encountered in situations where the plants grow closely to one another and tend to form a "closed canopy" of interlocking branches or limbs that tend to inhibit the passage of air therethrough. When this occurs, the leaves on a plant which are positioned generally above the "canopy" are exposed to the ambient air and receive a continually replenished supply of carbon dioxide. However, leaves which are located below the canopy must scavenge carbon dioxide from the air underneath the canopy. Since the canopy itself tends to limit recirculation of the air supply, the level of carbon dioxide beneath the canopy is reduced quite rapidly. Under many circumstances, such as those encountered in many forests, this tends to choke off the lower leaves and their associated branches, which effectively precludes any contribution to the growth of the plant as a whole from these lower leaves.

Although it would be possible to spray plants which grow into a closed canopy with an aqueous carbon dioxide solution, as suggested by the prior art, this would not be practical for many applications. This approach would be particularly inappropriate for plants such as trees wherein the cost of continuously spraying the entire plant with the solution could greatly outweigh the increased yield.

SUMMARY OF THE INVENTION

The present invention provides an economical and practical means of delivering gaseous carbon dioxide to plants growing under field conditions, and is particularly well suited for use in connection with a plant environment that defines a closed canopy. The invention can have immediate, significant commercial impact on the reforestation of land, and in increasing yield and shortening the harvest rotation in fields devoted to commercial forestry.

The invention comprises an elongate trench within which the vegetation to be harvested may be planted. Although the type and density of vegetation grown in the trench may be varied as desired, plants are preferably planted in an over-stocked condition and permitted to grow sufficiently to define a closed canopy. Gas enriched with carbon dioxide may then be supplied to the trench beneath the level of the canopy.

The carbon dioxide-rich gas may be supplied to the trench by means of one or more conduits. In one preferred embodiment, the conduit means simply deliver gas adjacent one end of the trench, and the trench is provided with a slope generally downwardly away from that end of the trench. This permits the carbon dioxide gas, which is denser than ambient air, to flow from a location near one end of the trench toward the other end of the trench. In another embodiment, elongate conduits may be placed within the trench and extend generally along the length of the trench to release carbon dioxide through a plurality of ports. In both embodiments, the carbon dioxide is desirably delivered to the trench at a location between the floor of the trench and the closed canopy of the vegetation.

The trench desirably includes a floor and a pair of sidewalls which extend along the length of the trench and slope generally outwardly away from one another in an upward direction. A plurality of such trenches may be employed with the trenches being oriented substantially parallel to one another and having a sidewall disposed immediately adjacent a sidewall of another trench. These adjacent sidewalls define elongate ridges elevated above the floor of the trench. The sidewalls and their associated ridges serve to restrict the flow of air beneath the canopy, minimizing the dilutive effects of the atmosphere. In a particularly preferred embodiment, the trench or trenches are oriented generally perpendicularly to the generally prevailing wind direction at the trench site.

DETAILED DESCRIPTION OF THE PREFERRED EMBODIMENTS

Figure 1:
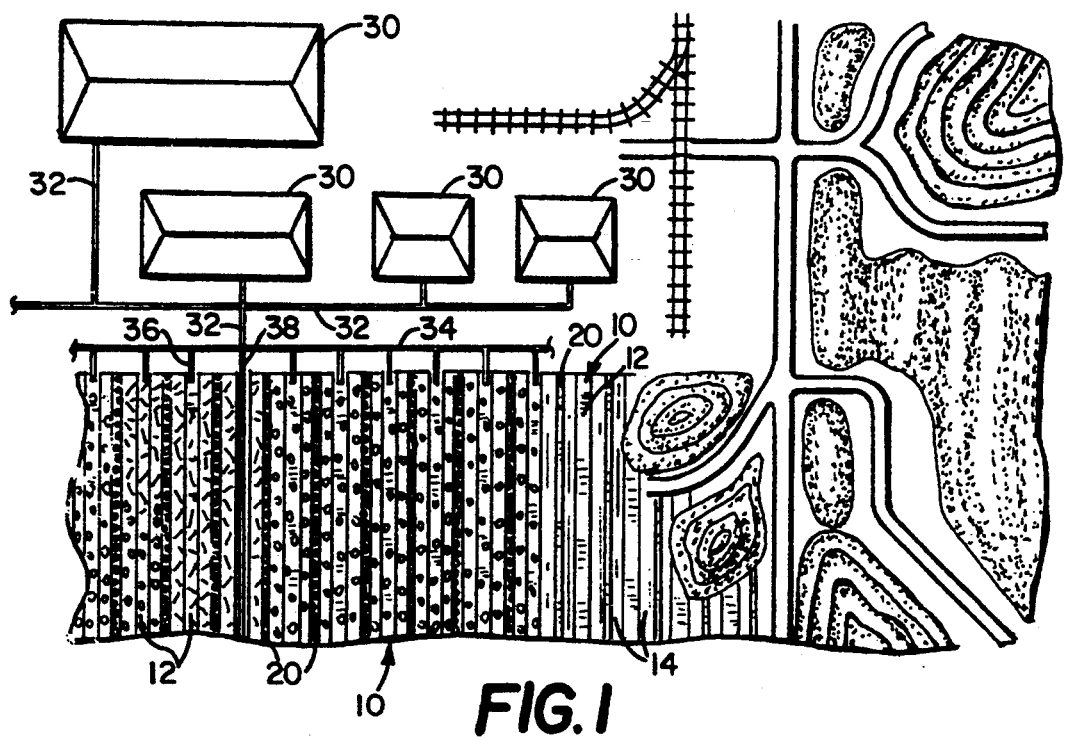
FIG. 1 is an aerial view of a plant growing system according to the present invention.
Figure 2:
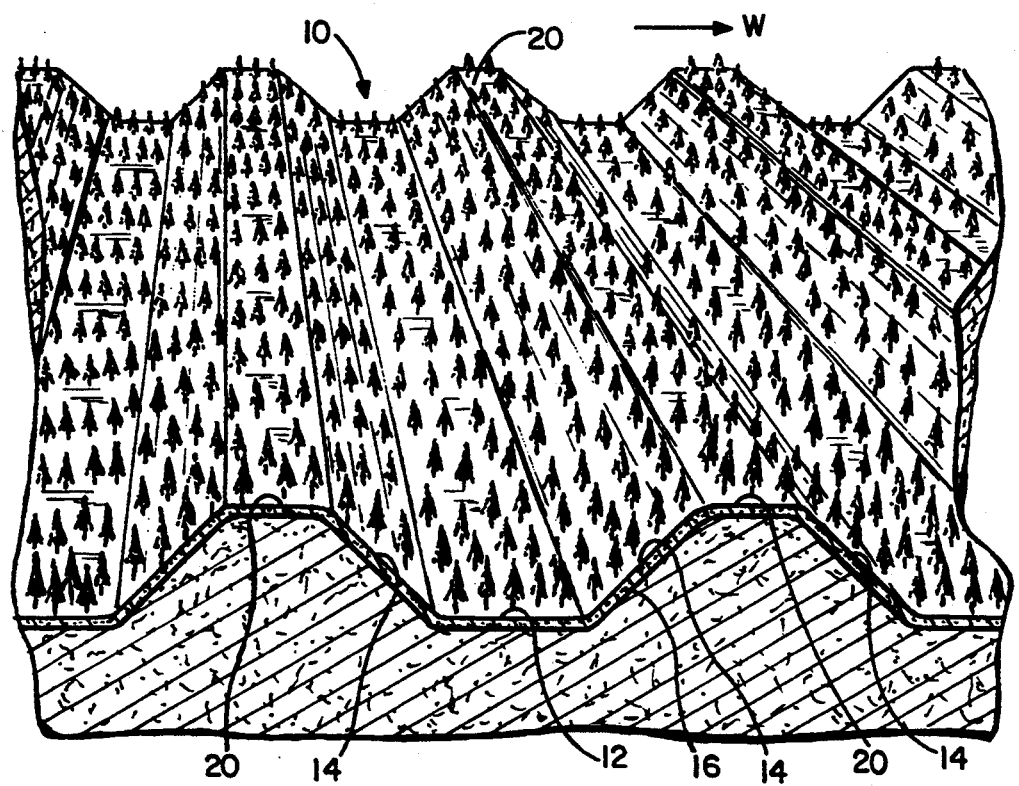
FIG. 2 is a partially cut away, perspective view of the invention of FIG. 1.
Figure 3:
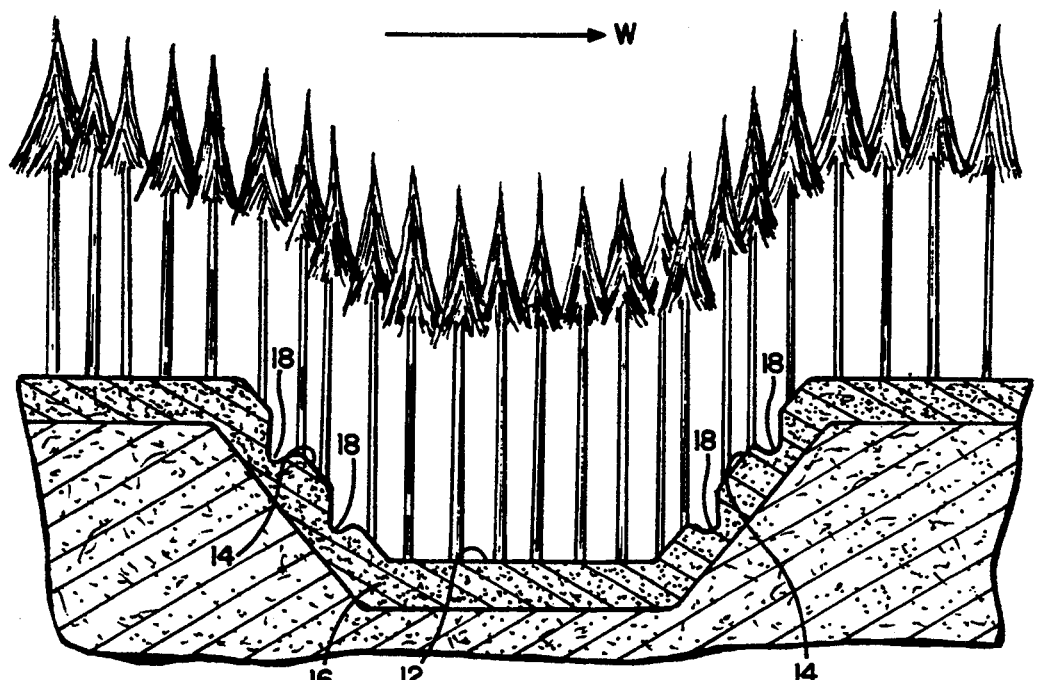
FIG. 3 is a cross-sectional side view of a trench of FIG. 1.

A system for enhancing plant growth according to the present invention is shown in FIGS. 1–3. The invention includes at least one elongate trench 10 in which a plurality of plants may be grown. The trench comprises a floor 12 and a pair of sidewalls 14 which extend along the length of the trench. The sidewalls desirably slope generally outwardly and away from one another in an upward direction. As will be described in more detail below, the sidewalls of the trench are designed to minimize loss of carbon dioxide from the environment of the trench; if the sidewalls are too short or the slope is too gradual, their ability to retain carbon dioxide within the trench will suffer. If the sidewalls are too steep, however, the effects of erosion will be more pronounced, adversely affecting their long-term stability. Although erosion can be checked by known means, such as employing a ground cover of smaller vegetation with extensive root systems, the slope of the sidewalls must be optimized by balancing these two competing considerations. Other factors, such as the nature of the soil and average rain fall at the site, must also be taken into consideration. Accordingly, the slope of the sidewalls will tend to be relatively site-specific.

If so desired, a layer of top soil 16 may be enriched with fertilizers, such as a nitrogen-rich fertilizer, or other known chemicals which are useful in enhancing the growth of vegetation or increasing its resistance to disease or parasites. Elongate ditches 18 may also be provided in the sidewall. These ditches may, for example, be used for irrigation or, as explained below, elongate conduits for delivering carbon dioxide to the trench may be placed within these ditches. Although a pair of trenches are shown spaced from the floor 12 and one another on each sidewall 14, the number and location of ditches may be varied as desired.

In a preferred embodiment, a plurality of such trenches 10 are provided, with the trenches being oriented generally parallel to one another. A sidewall 14 of each trench is positioned adjacent the sidewall 14 of another trench, with the adjacent sidewalls defining a ridge 20. Although the sidewalls may directly abut one another to define a narrow ridge at the apex of the sidewalls, the ridge is desirably somewhat wider and may be substantially horizontal, as shown. Such horizontal ridges not only help minimize erosion, but they also provide a suitable planting surface for additional vegetation which may act as a windbreak, serving to further reduce the wind currents. The plants grown on the ridge to create the windbreak may all be of the same variety, and at approximately the same stage of growth, but this is not preferred. Instead, it is desirable to provide a windbreak composed of both tall, mature plants, such as mature trees, and a variety of shorter plant life to more effectively shelter the trench from wind turbulence.

For reasons explained below in connection with the delivery of carbon dioxide to the trench, it may be desirable to provide a sloped floor 12. In a preferred embodiment, the floor slopes downwardly from one end of the trench toward the other at a gradient of between about 0% and about 10%. A gradient of about 10% was found to work well in a laboratory test (set forth below).

The trenches may be oriented as desired. Although the layout of the land may effectively dictate the direction of the trenches, they are preferably oriented generally perpendicularly to the "prevailing wind direction." Obviously, the precise direction of wind currents adjacent the trench will vary over time. However, the historic weather patterns of many areas indicate that weather systems, and hence wind, will more frequently tend to move in a certain general direction. This direction is referred to herein as the "prevailing" wind direction, and is indicated in FIGS. 2 and 3 by the arrow designated "W."

Orienting the trenches such that they extend generally perpendicularly to this prevailing wind direction improves retention of carbon dioxide within the trench. If the wind travels in a direction substantially parallel to a trench, it will carry carbon dioxide-rich air within the trench along the length of the trench and out one end thereof. As the wind direction approaches from a direction substantially perpendicular to the length of the trench, though, the sidewalls 14 and the windbreak, if any, on the ridges 20 impede the flow of air into the trench. By so restricting the passage of air into and through the trench, the sidewalls and the ridges serve to prevent the carbon dioxide-rich air which is supplied to the trench from being either diluted by or carried off with the ambient air.

FIGS. 1–3 depict the trenches of the present system as being substantially straight along their length. While the depicted construction is preferred, the invention may be practiced in trenches which may significantly deviate from a straight path.

The invention is particularly well suited to use in reforestation of denuded tracks of land. For example, in the process of strip-mining minerals, such as coal, the soil above the mineral deposit is systematically pushed aside to provide access to the deposit. In so doing, large, elongate mounds of the cleared earth are commonly formed. Those carrying out such mining are required by law (see, e.g., 30 U.S.C. §1201 et. seq.) to reclaim the land, i.e., to repopulate the site with vegetation, after the mining is completed. 91 Stat. 445 30 U.S.C. §1201 et seq. Surface Mining Control and Reclamation Public Law 95-87 Aug. 3, 1977. The current standard practice in the industry is to redistribute these elongate mounds to more or less recreate the original contour of the land and then plant vegetation on this new landscape.

Strip-mining sites may instead be modified to practice the instant invention. An elongate mound of cleared earth produced in the mining process may be formed to define a ridge 20 and the adjacent sidewalls 14 of two trenches of the invention. When two or more such ridges are so formed, suitable trenches may be defined. In the short term, this would be beneficial in that the cleared earth would not have to be as extensively redistributed from the series of long mounds. In the long term, this would transform the former site of a mine from a commercially-unproductive eyesore into a productive tract of land. In particular, the land may be planted with trees which can be sold as timber or as a raw material for forming pulp or combustible fuels, rather than merely lying fallow.

As noted above, a trench of the invention is provided with a supply of carbon dioxide-rich gas to accelerate growth of the plants in the trench. It was also previously explained that the average concentration of carbon dioxide in the ambient atmosphere is in the order of 0.03%, or 300 ppm. It is an object of the present invention to augment this concentration to at least about 0.15–0.20% (1500–2000 ppm). Although this concentration may be increased significantly more than that, if carbon dioxide comprises 10% (100,000 ppm.) of the ambient air, this may be toxic to animals which may live in the trench and workers who tend the trench. Furthermore, the beneficial effects of the heightened carbon dioxide concentration on plant growth are believed to diminish at concentrations of about 5% or more. Hence, it is preferred that the carbon dioxide concentration in the air within the trench be maintained at a level between about 0.15% to about 5%, with a range of about 0.20% to about 2% being preferred.

It is well known that at standard temperature and pressure, carbon dioxide gas is denser than atmospheric air. In particular, the density of carbon dioxide gas is approximately 1.5 times that of an average ambient air composition. Accordingly, if one were to release a gas having a high concentration of carbon dioxide into the trench adjacent the floor 12, this denser gas would tend to stay within the trench absent any disturbance by air currents. Thus, the sidewalls 14 and the vegetation, if any, planted on the ridge 20, serves an important function—by limiting wind turbulence in the trench, the loss of carbon dioxide from the trench is minimized. Under high-velocity wind conditions, though, these measures alone may prove to be insufficient to contain the carbon dioxide in a trench for an extended period of time. This is particularly true when vegetation in the trench is dispersed because the plants which are being treated with the carbon dioxide-rich gas will not actively prevent the loss of carbon dioxide.

In a preferred embodiment, the plants grown in a trench of the invention are "overstocked," i.e., they are planted more closely together than their optimum spacing under normal conditions. This will encourage the formation of a "closed canopy" as the upper portions of the plants grow rather close together. In the case of trees, for example, the upper branches of adjacent trees may tend to become interlaced with one another if the trees are planted too closely together. As explained above, such a closed canopy tends to result in the depletion of carbon dioxide from the air beneath the canopy because the supply of replenishing air is restricted by the presence of this closed canopy. Whereas the closed canopy restricts the flow of fresh air supplies to the underside of the canopy, this same restriction of gas flow through the canopy will trap carbon dioxide-rich gas in the trench.

Although a wide variety of plants may be grown in a trench of the invention, trees which grow well under overstocked conditions are generally preferred. Such trees include, for example, salixaceae populas tremuloides (quaking aspen). Alternatively, sorgham, a grain, may be used instead, as it has shown an ability to grow well when heavily stocked.

Carbon dioxide may be supplied to the trench by a wide variety of methods. In a preferred embodiment, depicted in FIG. 1, at least one source of carbon dioxide gas 30 (schematically depicted as a building in FIG. 1) delivers gas to the trench through conduit means 32. If more than one trench is formed at the site, the conduit means 32 may include a manifold 34 for controllably distributing the gas to each of the trenches.

The conduit means may deliver gas consisting essentially of only carbon dioxide. However, as explained above, carbon dioxide can be toxic to animal life at a concentration of about 10%. If such highly-concentrated carbon dioxide gas were to be delivered into the trench, this would both create a minimal gradient of carbon dioxide concentration along the length of the trench, and may present toxic levels of carbon dioxide adjacent the conduit means. It is preferable, therefore, to deliver at higher volumes to achieve the desired concentration within the trench. Both the flow rate and the concentration of carbon dioxide in this carbon dioxide-rich gas supply may be varied according to known principles in order to effectively ensure that the desired concentration is achieved, and that the carbon dioxide concentration is substantially constant along the length of the trench.

In one preferred embodiment, the conduit means includes a spur 36 which extends between the manifold 34 and a position adjacent the first end of the trench. This spur may simply discharge the carbon dioxide-rich gas directly into the trench, but it is preferred that a series of baffles (not shown) or the like be provided adjacent the discharge end of the spur to more effectively spread the gas supply across the floor of the trench. Alternatively, each trench may be supplied by a plurality of spurs 36 which are spaced horizontally across the width of the floor 12 of the trench. If conduit means according to the present embodiment are utilized, it is desirable that the floor of the trench slope generally downwardly in a direction away from the spur 36, as noted above. Since carbon dioxide is heavier than air, this will lead to a more uniform distribution of carbon dioxide along the length of the trench, because the carbon dioxide will tend to flow downhill, i.e., away from the spur 36. If so desired, this tendency may be enhanced by increasing the density of the gas exiting the spur, such as by cooling the gas by maintaining it under relatively high pressures in the conduit means 32.

In another preferred embodiment, the spur 36 of the previous embodiment is replaced with a supply duct 38 which may extend along substantially the entire length of the trench 10. The supply duct may be provided with a number of discharge ports (not shown) which are substantially equally spaced along the length of the supply duct to more evenly distribute the carbon dioxide-rich gas along the length of the trench. If the trench 10 includes a ditch (FIG. 3), the supply duct 38 may rest in a ditch. If so desired, more than one supply duct 38 may be provided in a trench, but it is not believed that this will be necessary under normal circumstances.

The carbon dioxide supply 30 is represented in FIG. 1 by a plurality of buildings. Although any suitable source of a carbon dioxide-rich gas may be used, buildings are shown in FIG. 1 to indicate that the carbon dioxide utilized in the invention may be a byproduct of any one or more of a variety of industrial processes. For instance, the carbon dioxide may be simply the byproduct of the anaerobic digestion of waste products, such as that set forth in U.S. Pat. No. 4,897,195, also owned by the present inventor. Ethanol is once again gaining increased acceptance as an alternative combustion fuel source, due to environmental concern and political instability of oil-producing nations. Since the process of producing ethanol from vegetation commonly gives excess carbon dioxide, this waste carbon dioxide from the fermentation process may be directed into trenches which are used to grow the very vegetation from which the ethanol is produced.

Figure 4:
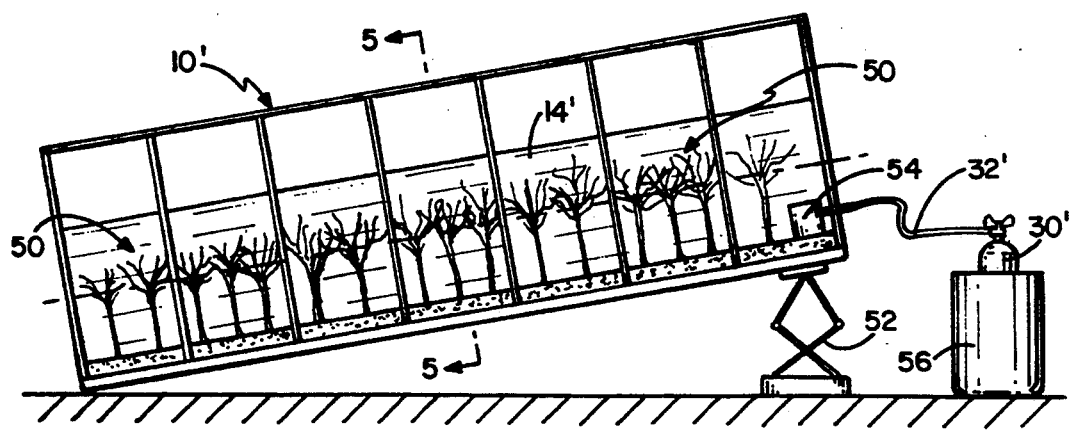
FIG. 4 is a side view depicting an experimental apparatus used to test the present invention.
Figure 5:
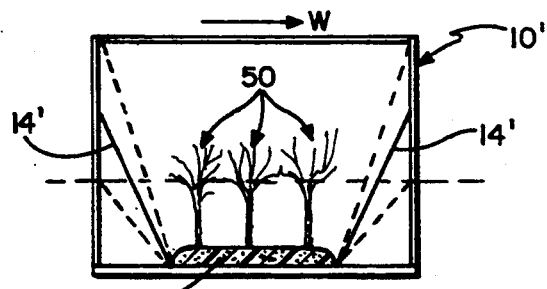
FIG. 5 is a cross-sectional view of the apparatus of claim 4 taken along section line 5—5.

An experimental, laboratory-scale apparatus which was used to test the viability of the invention is shown in FIGS. 4 and 5, wherein structure similar to that in FIGS. 1-3 bear like reference numerals with an addition of a prime ('). A trench 10' having a length of 20 feet, a width of four feet and a height of about three feet was formed in a skeletal form from a series of wooden planks. The sidewalls 14' simply comprise an elongate plastic sheet which can be raised or lowered to any height above the bottom of the trench 10' between about zero feet and about three feet (as indicated by phantom lines in FIG. 5). A series of plastic plants 50 was embedded in an elongate piece of a foam plastic material, which defined the floor 12' of the trench 10'. The plastic plants were placed in this styrofoam floor 12' in a relatively dense configuration, being 3-4 plants abreast. Although living plants could have been used, the purpose of the present test was simply to determine the operability of the carbon dioxide delivery system in a trench of the invention under field conditions (the increased growth rate of plants at higher carbon dioxide concentrations has already been sufficiently proven in the prior art).

This trench was supported adjacent one end by a hydraulic lift 52 which was used to vary the grade of the floor of the trench. This grade was varied in 5% increments between about 0% and approximately 15%. The carbon dioxide supply 30' of this laboratory apparatus comprised a standard pressurized tank of carbon dioxide gas which was fitted with a regulator device to carefully monitor the flow rate of the gas exiting the tank. The conduit means 32' comprised a rubber hosing which lead from the tank 30' to a box 54 which was placed adjacent the upper end of the sloped floor 12'. The box 54 included a plurality of baffles which served to evenly distribute the gas horizontally across the width of the floor 12'. The tank 30' was placed in a receiving vessel 56, and ice was placed within the vessel with the tank to cool the contents of the tank. A plurality of common electric fans (not shown) were placed along one side of the trench and were aligned to deliver air in a direction substantially perpendicular to the length of the trench in order to simulate the effects of wind approaching in the prevailing wind direction W. The concentration of carbon dioxide in the gas beneath the canopy C defined by the plants was measured with a Fyrite II combustion efficiency analyzer, which is commercially available from Bacharach Inc. The concentration of both oxygen and carbon dioxide was measured at distances from the upper end of the trench of 5 feet, 10 feet, 15 feet, and 20 feet (i.e., the end of the trench). In the experimental runs which included a "prevailing wind" created by the electric fans the speed of that wind above the canopy created by the artificial plants was measured with a conventional wind speed detector.

EXAMPLES

Carrying out the procedure outlined above, numerous experimental runs were made on the apparatus depicted in FIGS. 4 and 5. For example, the following generally illustrate the results of these tests.

EXAMPLE I

In a first test, the trench 10' was set at a 10% grade, and the sidewalls 14' were set at a heighth of 3 feet. The wind speed adjacent the top of the artificial plants 50 varied along the length of the trench from about 4 to about 10 m.p.h., with an average speed of 5.75 m.p.h. The carbon dioxide concentration in the supply gas, as measured within the baffles 54 was measured at about 11.8%, and the carbon dioxide concentrations 5 feet, 10 feet, 15 feet, and 20 feet from the baffle 54 was 4.7%, 4.9%, 4.2%, and 4.4%, respectively. Thus, the carbon dioxide concentration beneath the canopy was relatively constant along the length of the trench 10'. Accordingly, it can be concluded that the 3-foot sidewall and a gradient of 10% from one end of the trench to the other is sufficient to withstand significant wind speeds, at least if the wind approaches in a direction substantially perpendicularly to the length of the trench.

EXAMPLE II

A second experiment was run under similar conditions: The gradient of the floor 12' was about 10%, and the wind speed was between about 4 and about 8 m.p.h., with an average speed of about 4.9 m.p.h., and the wind direction was generally perpendicular to the length of the trench. In this experiment, however, the heighth of the sidewall 14' was reduced from 3 feet to about 2 feet. In this run, the carbon dioxide concentration of the supply gas was approximately 14.8% while the concentration was about 4% at 5 feet, 3.7% at 10 feet and 3.6% at both 15 and 20 feet. Thus, somewhat more of the carbon dioxide was lost to the air above the canopy in this experiment than was lost in the previous experiment. Even so, there was an even distribution of carbon dioxide concentration along the length of the trench, indicating that the 10% slope is sufficient to permit the carbon dioxide-rich gas to flow down the length of the trench under gravity.

EXAMPLE III

In another experiment, the floor 12' of the trench was substantially horizontal (i.e., a grade of about 0%) and the sidewall was lowered to the level of the floor 12'. These experimental parameters are representative of the condition commonly encountered under normal field conditions, on land that does not include the trench according to the present invention. Even though there was no wind current applied by the electric fans, the carbon dioxide concentration dissipated very rapidly—the inlet gas had approximately 11.6% carbon dioxide, but the level measured 5 feet from the baffle 54 was only 3.3%. The level measured at 10 feet was not accurately quantifiable due to technical limitations of the equipment employed.

Thus, this leads to the conclusion that simply supplying a gaseous carbon dioxide source to a common agricultural field which is not enclosed by a greenhouse or the like is impractical, because the carbon dioxide simply dissipates too rapidly. It should also be noted that these results were obtained even in the absence of any wind; one would expect the carbon dioxide to dissipate even more rapidly in the presence of a significant wind current.

The data from these illustrative experiments and a number of other experimental runs makes it possible to draw some general conclusions about the preferred structure of a trench according to the present invention, at least in the embodiment wherein the carbon dioxide-rich gas is supplied adjacent one end of the trench. In that embodiment, it would appear that a gradient of approximately 10% for the floor 12 from one end to the other encourages the best distribution of carbon dioxide along the length of the trench 10. It is readily apparent that the sidewalls 14 played a large role in retaining the gas within the trench. Although the effects of erosion must be taken into account under field conditions, as noted above, as a general rule it would appear that the greater the height and slope of the sidewalls, the more effective they are in retaining the gas in the trench. Finally, from experiments conducted with a less dense stocking of plants, it appears that the closed canopy provides a rather effective barrier and enhances retention of the carbon dioxide-rich gas.

While a preferred embodiment of the present invention has been described, it should be understood that various changes, adaptations, and modifications may be made therein without departing from the spirit of the invention and the scope of the appended claims.

I claim:

1. A system for enhancing plant growth under field conditions comprising an elongate earthen trench having a floor and elevated side walls and having vegetation within said trench, and a carbon dioxide delivery system comprising a source of carbon dioxide-rich gas and conduit means delivering said gas to the trench.

2. The system of claim 1 wherein said trench is oriented generally perpendicularly to the prevailing wind direction.

3. The system of claim 1 wherein the conduit means delivers said gas adjacent one end of the trench.

4. The system of claim 3 wherein the floor of the trench slopes generally downwardly in a direction away from said conduit means.

5. The system of claim 1 wherein said conduit means includes an exhaust port adapted to deliver the carbon dioxide-rich gas adjacent the floor of the trench.

6. The system of claim 1 further comprising vegetation growing on the floor of the trench defining a canopy spaced above the floor.

7. The system of claim 6 wherein the conduit means includes an exhaust port adapted to deliver the carbon dioxide-rich gas at a location vertically disposed between the canopy and the floor.

8. The system of claim 1 wherein said sidewalls are angled generally outwardly away from one another in an upward direction.

9. The system of claim 8 further comprising a plurality of such trenches oriented substantially parallel to the first trench, with a sidewall of each trench being disposed immediately adjacent a sidewall of another trench, said adjacent sidewalls defining elongate ridges.

10. The system of claim 9 further comprising vegetation carried adjacent an upper portion of the ridge for minimizing wind turbulence within the trench.

11. A method of enhancing growth of vegetation in a field comprising the steps of planting vegetation in a trench having a floor and elevated sidewalls, said trench being oriented generally perpendicularly to the prevailing wind direction, permitting said vegetation to grow sufficiently to define a canopy spaced above the floor of the trench, and supplying carbon dioxide-rich gas by conduit means to the trench between the floor and the canopy.

12. The method of claim 11 further comprising the steps of planting vegetation in a second trench after planting vegetation in the first trench, the second trench having a floor and elevated sidewalls and being positioned substantially parallel to the first trench, permitting the vegetation in the second trench to grow sufficiently to define a canopy spaced above the floor of the second trench, and supplying carbon dioxide-rich gas by conduit means to the second trench between the floor and the canopy of that trench.

13. The method of claim 11 further comprising the step of providing a nitrogen-rich layer of soil along the floor of the trench before planting the vegetation in the trench.

14. The method of claim 11 further comprising the step of planting vegetation adjacent a portion of each elevated sidewall at a location disposed away from the floor of the trench to define a windbreak.

15. The method of claim 12 further comprising the step of planting vegetation along a ridge between the first and second trenches, one sidewall of the first trench being positioned adjacent a sidewall of the second trench to define said ridge.

* * * * *